United States Patent [19]

Brown

[11] Patent Number: 5,036,859

[45] Date of Patent: Aug. 6, 1991

[54] MOISTURE DETECTOR AND INDICATOR

[75] Inventor: Keith A. Brown, Coos Bay, Oreg.

[73] Assignee: Travis International, Inc., Coos Bay, Oreg.

[21] Appl. No.: 246,402

[22] Filed: Sep. 19, 1988

Related U.S. Application Data

[63] Continuation-in-part of Ser. No. 224,300, Jul. 26, 1988, abandoned.

[51] Int. Cl.$^5$ .............................................. A61B 5/20
[52] U.S. Cl. .................................. 128/734; 128/638; 128/886; 340/573
[58] Field of Search .............. 128/734, 638, 885, 886; 340/573

[56] References Cited

U.S. PATENT DOCUMENTS

| | | | |
|---|---|---|---|
| 2,866,454 | 12/1958 | McKenzie | 128/886 |
| 2,874,695 | 2/1959 | Vaniman | 128/138 R |
| 3,245,068 | 4/1966 | Wegryn et al. | |
| 3,460,123 | 8/1969 | Bass | 128/138 A |
| 3,530,855 | 9/1970 | Balding | 129/418 |
| 3,581,208 | 5/1971 | Buehrle et al. | 325/64 |
| 3,588,858 | 6/1971 | Demuth | |
| 3,678,928 | 7/1972 | Mozes | 128/138 |
| 3,696,357 | 10/1972 | Kilgore | 128/886 |
| 3,809,078 | 5/1974 | Mozes | 128/138 A |
| 3,832,993 | 9/1974 | Clipp | |
| 3,972,320 | 8/1976 | Kalman | |
| 4,106,001 | 8/1978 | Mahoney | 340/573 |
| 4,191,950 | 3/1980 | Levin et al. | 340/604 |
| 4,205,671 | 6/1980 | Lassen | 128/138 A |
| 4,205,672 | 6/1980 | Dvorak | 128/138 A |
| 4,212,295 | 6/1980 | Snyder | 128/138 A |
| 4,539,559 | 9/1985 | Kelly et al. | 340/573 |
| 4,640,276 | 2/1987 | Jing-Sheng | |
| 4,675,656 | 6/1987 | Nareisse | 128/903 |
| 4,736,752 | 4/1988 | Munck et al. | 128/798 |
| 4,738,260 | 4/1988 | Brown | 128/138 A |
| 4,754,264 | 6/1988 | Okada et al. | 340/573 |
| 4,795,456 | 1/1989 | Borgers et al. | 604/389 |
| 4,800,370 | 1/1989 | Vetecnik | 128/886 |

FOREIGN PATENT DOCUMENTS 2529080 6/1982 France.

OTHER PUBLICATIONS

Page 534 from Sears Catalog (Items 6 and 7) for Bed-Wetting Alarms.
Page 693 from J. C. Penney Catalog for Bedwetting Alarm.
Sales Literature Entitled "Help for Bedwetting" from Palco Labs (6pp).
Sales Literature Entitled "Enuretic Alarm" from Nytone Medical Products, Inc. (2pp).
Sales Literature Entitled "Eastleigh II Enuresis Alarm System Program for Home Care Dealers" from Electronic Monitors, Inc. (5pp).

Primary Examiner—William E. Kamm
Assistant Examiner—Scott M. Getzow
Attorney, Agent, or Firm—Klarquist, Sparkman, Campbell, Leigh & Whinston

[57] ABSTRACT

An apparatus which detects urination by a user includes a urine sensing pad for placement over the pubic and/or perianal areas of a user. The sensing pad includes a pair of electrodes on a backing sheet, and an absorbent cover sheet which is glued or heat sealed to the backing sheet. An indicator box is carried by the user and coupled to the sensing pad for generating a digitally encoded signal when urine moistens the pad and completes a circuit which includes the electrodes. Either a local alarm or remote signal is triggered by the indicator.

4 Claims, 2 Drawing Sheets

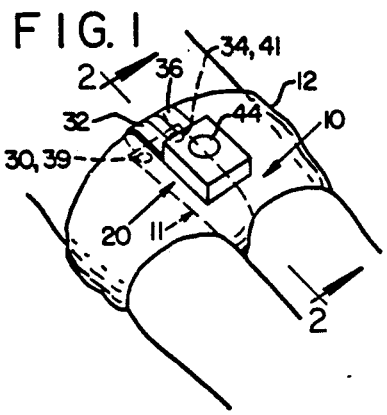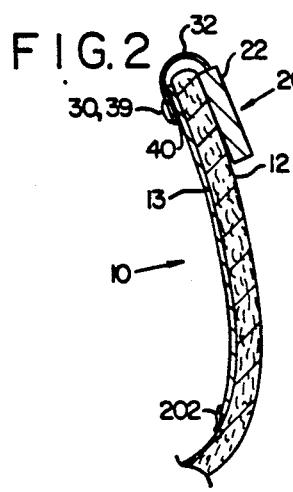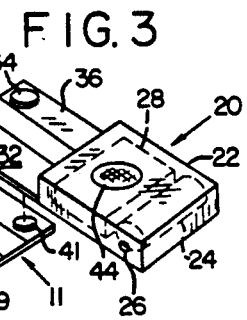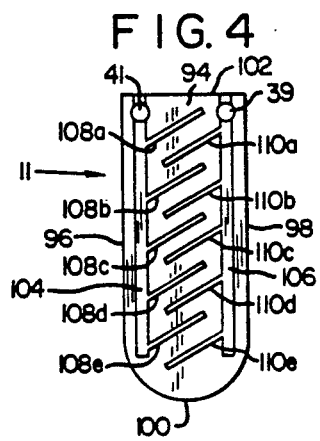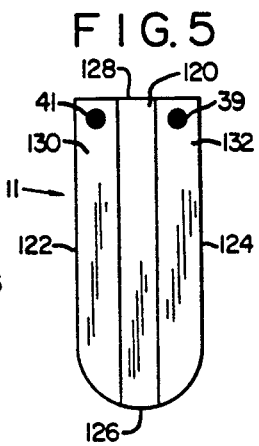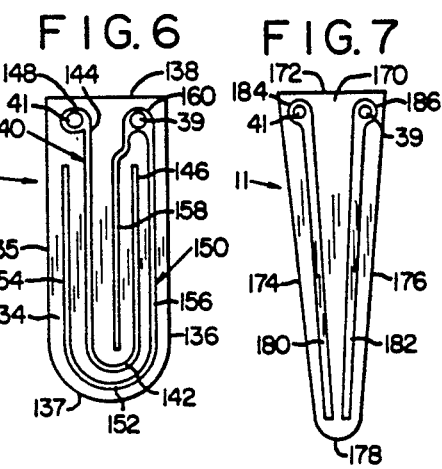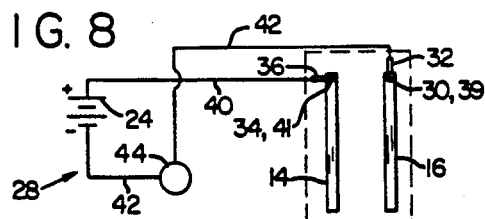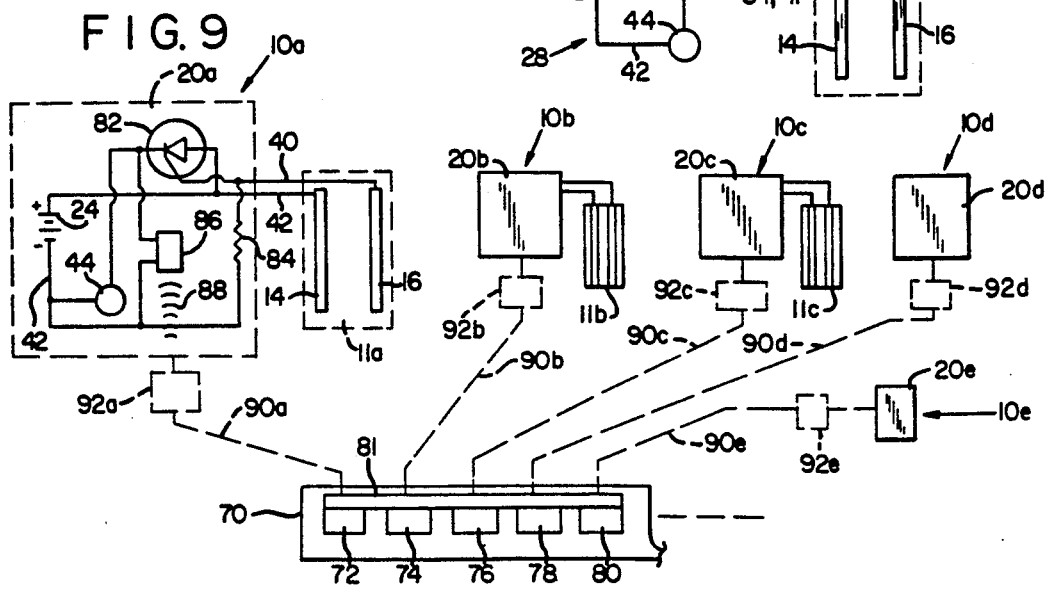

MOISTURE DETECTOR AND INDICATOR

CROSS REFERENCE TO RELATED APPLICATION

This is a continuation-in-part of application Ser. No. 224,300, filed July 26, 1988, now abandoned, invented by Keith A. Brown, and entitled WOUND LIQUID DISCHARGE DETECTOR AND PATIENT MONITORING SYSTEM.

BACKGROUND OF THE INVENTION

The present invention relates to a device for detecting unintentional urination by users, such as children during the night. The invention also relates to moisture sensing pads for sensing moisture from a user, with such pads, for example, being disposed adjacent the groin or perianal area of a user for detecting moisture.

A number of urine sensing or anti-bed-wetting devices have heretofore been employed to train enuretic children to awake in time to empty their bladders and avoid bed-wetting.

A common early approach consisted of placing metallic grids under a bed sheet, the grids being separated by absorbent but non-conductive materials such as cotton cloth. In such devices a flow of urine into the absorbent materials completes a circuit between the grids and activates a bedside alarm after urination. In this case, the previously non-conducting dry cloth is made conductive by the urine. These devices suffered from the disadvantage of a moderate delay between the onset of urination and the sounding of an alarm. This is particularly disadvantageous because the most effective training is achieved by waking an individual immediately by an alarm upon the onset of urination and prior to the time that the individual's bladder become substantially empty. There is also the inconvenience necessitated by changes of bed linen during the night.

In the past several years, different devices have been proposed which are portable and which have an electrode containing pad disposed in the groin area of a user. A conductive path is provided between the electrodes upon urination and an alarm sounds. These devices do decrease the time between the onset of urination and the triggering of an alarm and also have the advantage of at least theoretically reducing the amount of urine flowing into the bed.

However, such prior devices have suffered from a number of disadvantages. For example, some devices have been less than completely acceptable to many children because of the bulkiness of the devices in the groin area. Also, some prior devices employ a long length of rather stiff uncomfortable electrical cord coupled from a urine sensing pad in the groin area to an alarm, such as on the wrist or shoulder of the user. Another disadvantage of some previous devices is the use of a relatively small urine sensor in the groin area of a user. Such sensors are subject to being missed by flow of urine from a user and are thereby subject to failing to trigger an alarm. Also, other prior devices have electronic components and connectors which are exposed to highly corrosive urine.

Prior devices have also not been suitable for use in monitoring multiple children at home, or with patients in a hospital or nursing home. The alarms on such prior devices have typically sounded locally in the user's room where it could not be heard during the night by parents or medical personnel.

In addition, for children under about two years of age or incontinent individuals, it can be desirable not to have a local alarm triggered upon moisture emission by such individuals. Local alarms can unduly excite or traumatize these individuals. Yet, it is desirable to monitor these individuals so that their undergarments can be changed promptly when wet. Heretofore, devices used for monitoring children in pretoilet training years (i.e. up to age 2-3) from remote locations are unknown.

Therefore, a need exists for an improved device for detecting unintentional urination and also for improved moisture sensing pads for sensing the emission of bodily moisture.

SUMMARY OF THE INVENTION

The present invention is a urine sensor which is attached to a user for detecting flow of urine or other liquids from the user. The sensor includes first and second separated electrodes which form a portion of an electrical circuit path. The pressure of liquid between the electrodes completes the electrical circuit, and causes a transmitter to generate and send a digitally encoded signal which indicates that urination has occurred. The sensor preferably includes a flexible backing member with electrodes made of dried conductive ink. In some embodiments, an absorbent cover sheet overlies the electrodes and is heat sealed to the backing member.

It is accordingly one object of the present invention to provide an improved apparatus for detecting unintentional urination by a user of the apparatus, for preventing bed-wetting and for use in toilet training.

It is another object of the present invention to provide a moisture sensing pad for detecting the presence of urine or other moisture from a person upon the pad.

Another object of the invention is to provide such an apparatus which is suitable for monitoring multiple children at home, or multiple patients in a hospital or nursing home.

Yet another object is to provide such a device that is adaptable to either home or institutional use with children of different ages who are in different stages of learning to control urination.

A further object of the present invention is to provide an apparatus for detecting unintentional urination by a user, the apparatus having electrical components which are shielded from highly corrosive urine.

As still another aspect of the present invention, the device includes electrical circuit means which reliably sounds an alarm upon urine reaching the sensing pad.

As a further aspect of the present invention, one form of such circuit means includes a transmitter means for sending a coded digital signal upon the presence of urine on the sensing pad. A receiver means at a remote location triggers an alarm upon the reception of the encoded signal from the transmitter means.

As still another aspect of the present invention, the device is relatively inexpensive to manufacture, maintenance free, portable, light weight, durable, and reliable.

These and other aspects of the present invention will become apparent with reference to the following description and drawings.

BRIEF DESCRIPTION OF THE DRAWINGS

FIG. 1 illustrates an anti-bed wetting apparatus in accordance with the present invention shown in position within an undergarment worn by a user.

FIG. 2 is an enlarged, fragmentary view taken along lines 2—2 of FIG. 1.

FIG. 3 is a fragmentary, top isometric view illustrating the attachment between a sensor and transmitter of the present invention.

FIG. 4 is a front elevational view of a first embodiment of the sensor of the present invention.

FIG. 5 is a front elevational view of a second embodiment of the sensor of the present invention.

FIG. 6 is a front elevational view of a third embodiment of the sensor of the present invention.

FIG. 7 is a front elevational view of a fourth embodiment of the sensor of the present invention.

FIG. 8 is an electrical schematic diagram of one form of the urination indicating circuit utilized in the apparatus of FIG. 1.

FIG. 9 is an electrical schematic diagram of another form of the urination indicating circuit utilized in the apparatus of FIG. 1.

DETAILED DESCRIPTION OF PREFERRED EMBODIMENTS

Figure 10:
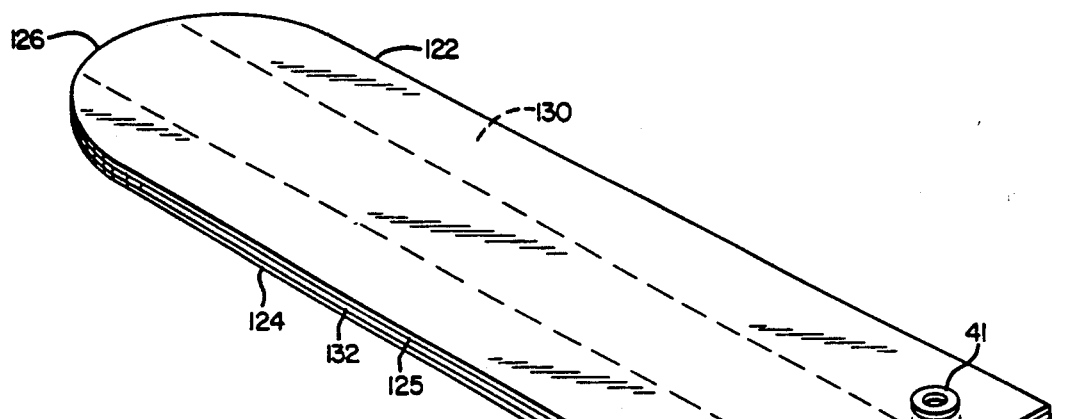
FIG. 10 is an enlarged, top isometric view of the embodiment of a sensor of the type shown in FIG. 5, illustrating respective layers of this form of sensor.

With reference to FIGS. 1 and 2, an apparatus for detecting urination by a user of the apparatus includes a urine detector 10 in which a sensing pad 11 is carried by the user within an undergarment 12, such as pajamas, underpants or a diaper. The pad is elongated, with a flexible backing 13, and can be disposable. The backing can, for example, be made of a moisture impermeable flexible material, such as polypropylene film or closed cell synthetic foam, or other material which is impermeable to urine and easily cleaned. Alternatively, the backing can be liquid absorbent paper or paper towel like material.

The pad 11 has first and second separated electrodes 14, 16 (FIGS. 3 and 5) extending longitudinally along opposing edges of backing 13. The illustrated electrodes 14, 16 are made of a liquid, electrically conductive material which is painted on or otherwise applied to backing 13. The liquid electrode material is allowed to dry or equivalently dried by dryers to form the electrodes. Electrodes made of conductive ink allow backing 13 to remain flexible. The conductive liquid material is preferably a conductive polymer ink, such as that sold by Acheson Colloids of Port Huron, Mich., under product designations SS24340 and SS24353.

An indicator unit 20 is attached to pad 11 and emits a signal when pad 11 is moistened. In the embodiment shown in FIGS. 1-3, the indicator unit 20 includes a housing 22 which holds a rechargeable nickel cadmium battery 24 and associated electrical circuitry. A charging socket 26 extends through a side wall of container 22 and provides access for a conventional battery charger to recharge battery 24. Housing 22 is typically made liquid impermeable by being dipped in a liquid which adheres to the housing. One such material is a plastic dip from PDI Inc. of Blain, Minn. Plastic dipping of housing 22 facilitates sterilization of indicator unit 20 by submersion or washing. The indicator unit 20 is also thus compact, self-contained and portable. Housing 22 may also, for example, be made of closed celled foam or other suitable material with an operable battery compartment for access to and replacement of a replaceable battery of the unit.

A pair of fasteners such as metallic snaps electrically connect the circuitry 28 (e.g., FIG. 8) to electrodes 14, 16. The metallic snaps include female snap member 30 at the end of an electrically conductive strip 32 and female snap 34 at the end of an electrically conductive strip 36. Of course, strips 32 and 36 may equivalently be replaced with suitable electrical conductive material, such as wire. Strips 32 and 36 may also be encased in plastic with electrical connection to the strips being accomplished by the snaps. Female snap 30 mates with a male snap 39, which pierces electrode 16 and is retained by backing 13 of the pad 11. Female snap 34 mates with a male snap 41 which pierces electrode 14 and is retained by the backing 13 of pad 10. These snap connections 30, 39 and 34, 41, respectively, electrically connect electrode 16 to strip or cord 32 and electrode 14 to strip or cord 36 such that completion of a circuit between electrodes 14, 16 will activate the detector in a manner described below.

Although FIG. 2 shows the cap of snap 30 facing toward the body of a person wearing the device, it is preferable that each of snaps 30, 34 be attached to strips 32, 36 such that snaps 30, 34 are insulated from the body. For example, the snaps 30, 34 should be located entirely between strips 32, 36 and backing 13 to prevent exposing the body to any electrical connections. Alternatively, an insulating member can be placed over the caps of snaps 30, 39 to cushion them and break electrical contact with the body. Finally, it would also be possible for the snaps 30, 39 and 34, 41 to be placed entirely between backing 13 and diaper 12 such that backing 13 insulates and cushions the snaps from the body.

In the embodiment shown in FIGS. 1-3, audible, visual and/or other indicating signals may be emitted when urine moistens the path between electrodes 14, 16 of pad 11. Alternatively, as explained below, such signals may be transmitted to a remote location for indicating the detection of moisture at this remote location, either alone or in conjunction with an indication locally at the user. One form of electrical circuit 28 for providing such discharge indicating signals is shown in greater detail in FIG. 8. A conductor 40 extends from the positive terminal of battery 24 to strip 36 and thereby to electrode 14, where it is attached to the electrode 14 by snaps 34, 41. Similarly, a conductor 42 is coupled from the negative terminal of battery 24 to strip 32 and thereby to electrode 16, where it is attached to the electrode 16 by snaps 30, 39. In FIGS. 3 and 8, a commercially available buzzer 44 is located along the circuit path including conductor 42 and is energized when the circuit shown in FIG. 8 is completed by moisture between electrodes 14, 16. As a result, when liquid is discharged from a user onto pad 11, the buzzer 44 will sound to alert the user (or medical personnel) that the wearer has urinated. The buzzer 44 in the preferred embodiment is plastic, and is available from Star Micronics, under the designation RMV-12 Buzzer. Buzzer 44 can be replaced by or supplemented with other indicator systems such as indicator lights or remote alarms as described later in connection with FIG. 9.

Another embodiment of the detector is shown in FIG. 9 in which the indicator sends a signal to a remote alarm. An optional local buzzer 44 or light may also be used. To avoid trauma to incontinent individuals or children who are too young to be trained, the local alarm is typically eliminated. In such a case, an alarm or indication of wetness will occur at a remote location, as explained below, and not on the user. As FIG. 9 illustrates, a number of separate detectors 10a, 10b, 10c, 10d, 10e, and so forth, can be used simultaneously. Each detector includes an indicator unit 20a-e and an associated sensor pad (11a-c being shown). In this embodiment, more than one sensor pad can be in use simultaneously for each user, with each sensor being placed in liquid sensing proximity to an external urethral orifice, for example, in the pubic or perianal area, of the user. Also, multiple sensors may be used with different sensors being carried associated with different persons who are being monitored by the detector. The capability of using multiple sensors allows the use of detectors 10 in institutions such as day care centers, hospitals or nursing homes, where individuals are monitored by nurses or attendants at a common control panel or receiver unit 70 at a monitoring location. Alternatively, the detectors are suitable for home use, for example, for use in monitoring a number of children at home.

Control panel 70 contains indicator lights 72, 74, 76, 78 and 80 or other alarms corresponding to individual detectors 10a-e attached to different persons. When one or more of the patients urinates, the appropriate detectors 72-80 are energized by an output signal from a receiver 81 to identify persons who have urinated such that their clothes or bedding can promptly be changed.

As described in greater detail below, the FIG. 9 system preferably employs a transmitter in each indicator unit 20 which is associated with the respective one of the persons being monitored. Upon the detection of urination, the transmitters send indicating signals to one or more receivers 81 at the console 70. In response to the received signals, appropriate indicators are activated. Instead of transmitting signals directly to the console 70, the signals may be sent from the transmitters to associated relay locations (i.e., 92a, 92b, 92c, 92d and 92e). Receivers at the relay locations produce output signals upon the detection of moisture discharge indicating signals. These receiver output signals are then delivered, for example, over electrical conductors, to the console 70 for activation of the appropriate indicators 72-80.

In connection with the specific form of indicator unit shown in FIG. 9, the conductor 40 is connected to the gate of a silicone control rectifier or thyristor 82. The anode of thyristor 82 is connected to the conductor 42. Also, the cathode of the thyristor is connected to the negative terminal of battery 24. An optional light and/or buzzer 44 may be included in this circuit path, but typically is not. The sounding of a local alarm 44 can unduly excite a young child or others in the child's room. In addition, the conductor 40 is coupled through a resistor 84 to the conductor 42. The circuit of FIG. 9 also includes an encoder/transmitter 86 coupled between the cathode of the thyristor 82 and the negative terminal of the battery 24. With this circuit, upon the presence of an extremely small amount of urine or other liquid between the electrodes 14, 16, the thyristor 82 conducts and allows current to flow to the buzzer 44 (if present) and through transmitter 86. By using a thyristor, the amount of current delivered to the transmitter is not dependent upon the amount of current that flows between the electrodes 14, 16 once a threshold is reached. Therefore, a strong signal is automatically produced almost immediately when liquid is present between the electrodes 14, 16.

When the thyristor 82 conducts, current is delivered to the transmitter 86 and a signal, indicated by wave lines 88, is sent through the air to a receiver unit. The receiver unit is typically located at a location which is remote from the transmitter unit 86, for example, receiver 81 at a nurse's station 70 in a hospital or nursing home. Alternatively, receiver 81 can be located in a parent's room to monitor whether an infant or child at home has urinated and requires attention. The transmitter sends a digitally encoded signal to the receiver which decodes the signals. When, for example, the receiver unit detects the coded signal corresponding to detector 10a, an output signal is produced which causes the activation of an indicator light or alarm 72. This signals the reception of the coded signal via the receiver, and alerts parents, attendants or medical personnel to check on the user to determine if bed clothes or clothing need be changed. Moreover, the person having the detector 10a is identified by activation of indicator 72 so that parents or hospital personnel know which user to check. Similarly, other indicators 74-80 are activated by indicating signals from the transmitters of the other detectors 10b-e. The transmitter 86 and receivers 81 are commercially available. For example, a National Semiconductor LM1871 RC encoder/transmitter is suitable for each transmitter with the corresponding receiver. A multiple channel receiver can also be used.

With such a transmitter and receiver arrangement, a number of urination detection devices may be used at home, in a hospital, a day care center, or nursing home without interfering with one another. That is, each of the devices is designed to receive and send a distinctly different coded signal. Therefore, the various receivers are not inadvertently activated by spurious signals from other devices, or by other interfering signals such as from citizens band radios, other medical equipment, and the like. Medical personnel will therefore immediately be able to determine which of the sensors 10a, 10b, 10c, 10d, 10e and so on has been activated, and can promptly respond by examining the appropriate person.

In an alternative embodiment also indicated in FIG. 9, the detectors 10a, 10b, 10c, 10d, 10e are connected to receiver 70 by conductors 90a, 90b, 90c, 90d and 90e, respectively. In this case, the transmitter sends the digital encoded signals over the conductors to the receiver. Such "hard wire" connections avoid the necessity of sending signals through the air in an institutional environment where such signals might interfere with the proper functioning of other medical equipment. However, the "hard wire" embodiment is not very practical in environments, such as day care centers, where users of sensors are highly mobile.

In yet another form of a system of the invention, conductors 90a-90e are not directly connected from the console 70 to the detectors. Instead, transmitter 86 in receiver 10a sends a digitally coded signal through the air to a receiver at a signal relay location 92a located in a user's room or at some other nearby location. The receiver at the relay location responds to the received coded signal by delivering an output signal along a conductor 90a to the indicator 72 at console 70. Separate receivers 81 at relay locations 92b, 92c, 92d and 92e may be located in different patient rooms to receive signals respectively from the transmitters of detectors 10b, 10c, 10d and 10e. These receivers produce signals which are conducted along conductors 90b, 90c, 90d and 90e to the indicators 74, 76, 78 and 80, respectively. One advantage of using receivers at local relay locations is that weaker signals 88 are required to activate a local receiver than those required to activate a remote receiver. The weaker signals are less likely to interfere with other electronic equipment than stronger signals that must be used to activate a remote receiver a greater distance away.

Alternate embodiments of pad 11 are shown in FIGS. 4–7. In the embodiment of FIG. 4, pad 11 includes an elongated backing 94 having longitudinal edges 96, 98, an arcuate bottom edge 100 and a flat or straight top edge 102. The electrodes include first and second parallel electrodes 104, 106 which extend, respectively, adjacent and parallel to edges 96, 98 of pad 11. Electrode 104 includes a series of fingers or projections 108a, 108b, 108c, 108d and 108e, while electrode 106 includes a series of fingers 110a, 110b, 110c, 110d and 110e which extend from electrode 106 towards electrode 104, and interdigitate with fingers 108a–e of electrode 104. The interdigitating fingers 108a–e are parallel to the fingers 10a–e. The lesser included angle between electrode 104 and fingers 108a–e is about sixty degrees, and the lesser angle between electrode 106 and fingers 110a–e is also about sixty degrees. Male snap 41 pierces electrode 104 and backing 94 and is retained by backing 94 to establish an electrical connection between electrode 104 and the snap connector when snap 34 is coupled to snap 41. Male snap 39 similarly pierces electrode 106 and is retained by backing 94 to establish an electrical connection between electrode 106 and the snap connector. The interdigitating electrodes 108, 110 decrease the distance that must be bridged by liquid to complete the circuit and sound an alarm. This reduced distance between electrode sections increases the sensitivity of the detector. Also, the angled positioning of the electrode fingers relative to the edges of the backing allows virtually the entire sensor pad to be used in sensing moisture from a user.

Another embodiment of pad 11 is shown in FIG. 5, in which pad 11 includes an elongated backing 120 having longitudinal edges 122, 124, an arcuate bottom edge 126 and a flat top edge 128. Paired parallel electrodes 130, 132 are positioned, respectively, adjacent and parallel to edges 122, 124 of pad 11. Male snap 41 pierces electrode 122 and backing 120 and is retained by backing 120 for establishing an electrical connection between electrode 130 and the snap connector. Male snap 39 similarly pierces electrode 132 and is retained by backing 120.

The embodiment of pad 11 shown in FIG. 6 uses another electrode configuration which diminishes the distance between the electrodes to increase their sensivitity. Pad 11 includes a backing 134 having longitudinal edges 135, 136, an arcuate bottom edge 137, and a flat top edge 138. A first, inner electrode 140 is substantially U-shaped with a closed, curved end 142 and an opposite open end bounded by parallel electrode legs 144, 146 which are respectively parallel to longitudinal edges 135, 136. An enlarged terminal portion 148 of leg 144 is positioned adjacent to edge 138 and receives male snap connector 41. A second electrode 150 includes a U-shaped portion between electrode 140 and edges 135, 136 and 137. Electrode 150 has a closed curved end 152, and legs 154, 156 which are substantially parallel to legs 144, 146, respectively. Second electrode 150 additionally includes a third leg portion 158 which extends into the open end of the U formed by electrode 140. Third leg 158 runs parallel to legs 144, 146 and terminates adjacent to, but short of, portion 142 of electrode 140. Legs 156 and 158 of electrode 150 are joined by an electrically conductive enlarged area 160. Male snap 39 pierces area 160 to establish an electrical connection between the snap and electrode 150.

The embodiment of pad 11 shown in FIG. 7 is designed to fit comfortably in the pubic and perianal areas of a user. This design also increases the sensitivity of the detector by diminishing the spacing between the electrodes from top to bottom of the sensor. The pad includes an elongated, truncated triangular backing 170 having a flat top edge 172, inclined edges 174, 176, and a curved apical edge 178. A pair of electrodes 180, 182 extend longitudinally along pad 11 parallel to edges 174, 176, respectively. Electrodes 180, 182 incline towards one another along their lengths, being most distantly spaced from each other near top edge 172 and closest together at apex 178. The terminal portion of each electrode 180, 182 adjacent top edge 172 is enlarged to form a conductive area 184, 186, respectively, through which metal snaps 39, 41 are placed.

The triangular shape of the pad in FIG. 7 comfortably conforms to the pubic and perianal areas of a wearer. The short distance between electrodes 180, 182 near apex 178 reduces the amount of liquid urine which must moisten the pad between the electrodes to complete the circuit and sound an alarm.

FIG. 10 illustrates a three layered embodiment of pad 11 which is similar in shape to the pad shown in FIG. 5, and corresponding parts are given reference numerals similar to the pad in FIG. 5. Electrodes 130, 132 are painted on backing 120, dried and then covered by a liquid permeable or absorbent layer 125, such as absorbent paper, polyolefin sheet, or cotton cloth with a self-adhesive face, which sticks to backing 120 and electrodes 130, 132 when pressed against them. After the layers of the pad are assembled, snap 39 is secured in place through cover layer 125, electrode 132 and backing 120. Similarly, snap 41 is secured in place through cover layer 125, electrode 130 and backing 120.

Figure 11:
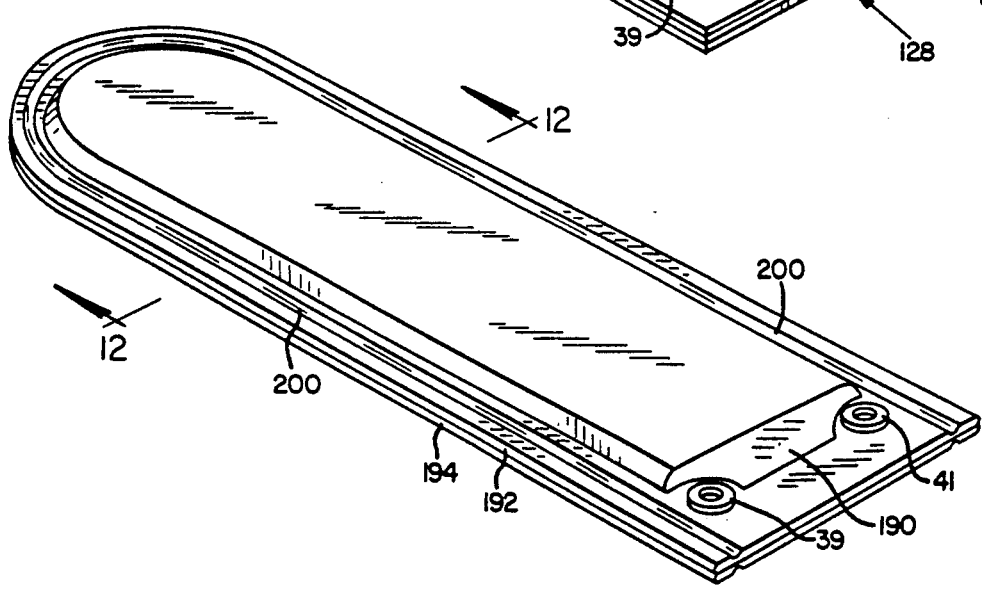
FIG. 11 is a top isometric view of another embodiment of the sensor of the present invention.
Figure 12:
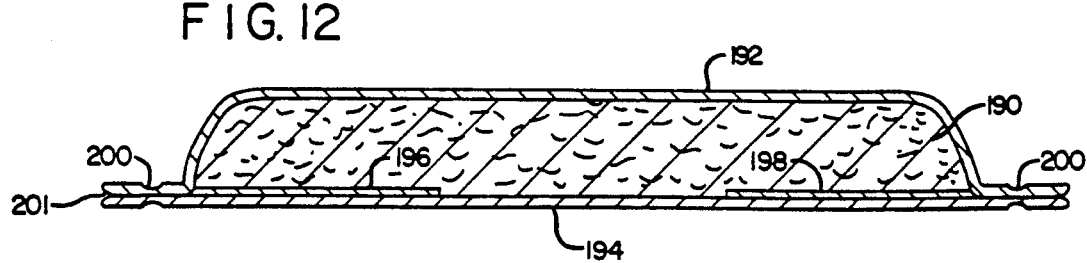
FIG. 12 is a cross sectional view, taken along section line 12—12, of FIG. 11.

The embodiment of the pad shown in FIGS. 11 and 12 is similar to that of FIG. 10, but it contains an additional absorbent layer 190 between a cover sheet 192 and backing sheet 194. As in the embodiment of FIG. 10, electrodes 196, 198 are painted on backing 194 and dried. A thick optional layer of highly absorbent material, such as natural or synthetic fibers, including cotton 190, is placed over the electrodes 196, 198. Absorbent cover sheet 192 is then positioned over absorbent layer 190, and sheets 192, 194 are sealed to one another along a U-shaped seam 200 around the sides and lower periphery of layer 190. Backing and cover sheets may be of heat fusible or heat settable materials, such as polyester and polypropylene, and heat sealed at seam 200. As shown in FIG. 12, the backing and cover sheets may be cut, for example, at 201, outside of the seam 200 so that a softer edge is provided to the pad to minimize irritation to a user.

In use, any of the pads 11 (FIGS. 4–7 and 11–12) are connected to indicator 20 by pressing together snaps 30, 39 and snaps 34, 41 to establish an electrical connection between the electrodes of pad 11 and the circuitry 28. Pad 11 is then placed within garment 12 over the pubic and perianal area with backing sheet (for example, 120 or 194) directed anteriorly. The electrodes will face posteriorly against the body of the user. A liquid permeable sheet (such as 125 in FIG. 10) or both a liquid permeable sheet and an absorbent layer (such as 190 and 192 in FIG. 12) is between the electrodes and body. If the user of the device urinates, the absorbent sheet and/or layer quickly soaks up the liquid and becomes electrically conductive to complete the circuit between the electrodes and activate alarm buzzer 44 or signal lights 72-80, or both.

As shown in FIG. 1, pad 11 is positioned over the pubic and perianal areas inside a diaper 12 with snaps 30, 39 and snaps 34, 41 near the waist portion of the diaper. The opposite end of pad 11 may optionally be secured to the inside face of diaper 12 with a piece of tape 202 or a pin (not shown). Strips 32, 36 are supported on a flexible flap connected to the housing for indicator 20. This flap is draped over the waist of diaper 12 so that indicator 20 hangs in front of the diaper (FIGS. 1 and 2). Indicator 20 can be secured in place against the outside face of diaper 12 with, for example, double-faced adhesive tape. The compact size of indicator 20 prevents it from annoying the user while he is sleeping.

Numerous other variations are possible. For example, connectors other than snaps 30, 39, 34, 41 can be used to make electrical contact with the electrodes 14, 16. The snaps can be replaced, for example, by alligator clips. Battery 24 can, moreover, be replaced by a source of 110 volt alternating current.

Although the disclosed embodiment of sensor 12 uses conductive ink electrodes, other materials may be used for the electrodes. For example, the electrodes can be layers of foil glued to one or both faces of backing 13. Alternatively, strips of metallic paint can serve as the electrodes. The electrodes can be arranged in any configuration, and may be placed at greater or lesser distances from one another to vary the sensitivity of detector 10.

The detector 10 is also suitable for sensing the presence of moistures from persons other than urine, for example, blood or bodily exudates.

When used to sense urination, detector 10 is especially useful in toilet training infants and preventing bed-wetting by older children. Bed-wetting is stopped, for example, if local alarm 44 sounds to awaken the user as soon as urine begins to flow.

Having illustrated and described the principles of my invention with reference to several preferred embodiments, it should be apparent to those persons skilled in the art that such invention may be modified in arrangement and detail without departing from such principles. I claim as my invention all such modifications as come within the true spirit and scope of the following claims.

I claim:

1. An apparatus for detecting urination by a user, the apparatus comprising:
   a urine sensor means adapted to be carried by said user for detecting urination by the use, the urine sensor means including first and second separated electrodes which form a portion of an electrical circuit path, the conductivity of the portion of the circuit path between the electrodes increasing upon the presence of urine between the electrodes;
   transmitter means adapted to be carried by said user and electrically coupled to said urine sensor means for generating and transmitting a digitally encoded signal in response to sensing by said sensor means of urine between said electrodes;
   said urine sensor means comprising a urine sensing pad having a backing which supports said first and second electrodes, said first and second electrodes comprising a dried electrically conductive polymer liquid positioned on the backing to define the first and second electrodes; and
   attachment means for detachably securing said transmitter means to said sensing pad and establishing electrical conductivity therebetween, said attachment means further comprising flexible extension means for allowing the positioning of said transmitter means to extend away from said sensing pad such that said transmitter means can be draped on the outside of a garment when said apparatus is in use.

2. The apparatus of claim 1 further comprising a diaper having an inner face and an outer face, said urine sensing pad being positioned against said inner face, and said transmitter means being positioned against said outer face.

3. An apparatus for detecting urination by a user, the apparatus comprising:
   a urine sensing pad means for placement in a garment worn by said user, said pad means including an absorbent which supports first and second separated electrodes which form a portion of an electrical circuit path, the conductivity of the portion of the circuit path between the electrodes increasing upon the presence of liquid between the electrodes;
   an indicator means encased in a sterilizable material and adapted to be carried by said user outside said garment for generating a digitally encoded signal in response to sensing by said sensing pad means of urine between said electrodes; and
   extension means for interconnecting and electrically coupling said pad means and indicator means such that said indicator means can be draped on the outside of said garment when said apparatus is in use.

4. An apparatus for detecting urination by a user, the apparatus comprising:
   a urine sensor means adapted to be carried by said user for detecting urination by the user, the urine sensor means including first and second separated electrodes which form a portion of an electrical circuit path, the conductivity of the portion of the circuit path between the electrodes increasing upon the presence of urine between the electrodes;
   transmitter means adapted to be carried by said user and electrically coupled to said urine sensor means for generating and transmitting a digitally encoded signal in response to sensing by said sensor means of urine between said electrodes; and
   attachment means for detachably securing said transmitter means to said urine sensor means and establishing electrical conductivity therebetween, said attachment means further comprising flexible extension means for allowing the positioning of said transmitter means to extend away from said urine sensor means such that said transmitter means can be draped on the outside of a garment when said apparatus is in use.

* * * * *